(12) United States Patent
Borst et al.

(10) Patent No.: US 10,851,391 B2
(45) Date of Patent: Dec. 1, 2020

(54) DRY-MILLING PROCESS

(71) Applicant: BASF SE, Ludwigshafen am Rhein (DE)

(72) Inventors: Joseph P. Borst, Wyandotte, MI (US); Anthony Newton, San Diego, CA (US); Kenneth L. Zack, Wyandotte, MI (US)

(73) Assignee: BASF SE, Ludwigshafen am Rhein (DE)

( * ) Notice: Subject to any disclaimer, the term of this patent is extended or adjusted under 35 U.S.C. 154(b) by 85 days.

(21) Appl. No.: 16/311,337

(22) PCT Filed: Jun. 20, 2017

(86) PCT No.: PCT/US2017/038299
§ 371 (c)(1),
(2) Date: Dec. 19, 2018

(87) PCT Pub. No.: WO2017/223068
PCT Pub. Date: Dec. 28, 2017

(65) Prior Publication Data
US 2019/0185885 A1 Jun. 20, 2019

Related U.S. Application Data

(60) Provisional application No. 62/352,263, filed on Jun. 20, 2016.

(51) Int. Cl.
*C12P 7/06* (2006.01)
*C11B 13/00* (2006.01)
(Continued)

(52) U.S. Cl.
CPC ............... *C12P 7/06* (2013.01); *A23K 10/38* (2016.05); *B01D 3/001* (2013.01); *C11B 13/00* (2013.01); *Y02E 50/10* (2013.01); *Y02W 30/74* (2015.05)

(58) Field of Classification Search
CPC C12P 7/06; A23K 10/38; B01D 3/001; C11B 13/00; Y02W 30/74; Y02E 50/17
See application file for complete search history.

(56) References Cited

U.S. PATENT DOCUMENTS

| 6,531,629 | B1 | 3/2003 | Eiermann et al. |
| 9,012,191 | B2 * | 4/2015 | Lee .................. C12M 21/12 435/161 |

(Continued)

FOREIGN PATENT DOCUMENTS

| WO | WO 2012/129500 A2 | 9/2012 |
| WO | WO 2012/142396 A1 | 10/2012 |
| WO | WO 2015/049345 A1 | 4/2015 |

OTHER PUBLICATIONS

International Search Report dated Sep. 21, 2017 in PCT/US2017/038299, citing documents AO, AP and AX therein, 4 pages.

(Continued)

*Primary Examiner* — Anthony J Weier
(74) *Attorney, Agent, or Firm* — Oblon, McClelland, Maier & Neustadt, L.L.P.

(57) ABSTRACT

A dry-milling process for the production of dried distiller's grains with solubles ("DDGS") includes the steps of dry-milling corn kernels to form a corn flour comprising corn fiber; combining the corn flour with water to form a mash; separating the corn fiber from the mash; treating the separated corn fiber with a composition; combining the treated corn fiber with the mash having the corn fiber separated therefrom to form a slurry; fermenting the slurry to produce beer and carbon dioxide; distilling the beer to produce ethanol and whole stillage; and processing the whole stillage to produce DDGS. The composition includes an alkanesulfonic acid, water, an enzyme, and optionally a surfactant.

23 Claims, 3 Drawing Sheets

(51) Int. Cl.
*A23K 10/38* (2016.01)
*B01D 3/00* (2006.01)

(56) References Cited

U.S. PATENT DOCUMENTS

| | | |
|---|---|---|
| 2008/0161591 A1 | 7/2008 | Richards |
| 2012/0244590 A1 | 9/2012 | Lee |
| 2012/0260938 A1 | 10/2012 | Zack et al. |
| 2015/0240266 A1 | 8/2015 | Lee |
| 2019/0322966 A1* | 10/2019 | Zack .......................... C12C 7/04 |
| 2019/0330576 A1* | 10/2019 | Borst ....................... C11B 13/00 |

OTHER PUBLICATIONS

Kotrba, R., "Gain free insight into new biodiesel, ethanol improvements", Retrieved from the internet: URL: http://www.biodieselmagazine.com/blog/article/2016/12/gain-free-insight-into-new-biodiesel-ethanol-process-improvements, XP002772545, Dec. 14, 2016, 1 page.

Fang-Hui, W., et al., "The Application and Research of Dispersing in Situ Nano-$SiO_2$ in Polyether Demulsifier TA1031", Journal of Dispersion Science and Technology, vol. 29, 2008, pp. 1081-1084.

\* cited by examiner

DRY-MILLING PROCESS

FIELD OF THE INVENTION

The present disclosure generally relates to a dry-milling process for the production of dried distiller's grains with solubles.

DESCRIPTION OF THE RELATED ART

The production of ethanol from corn can occur via two types of processes: (1) wet-milling processes, and (2) dry-milling (dry-grind) processes. Wet-milling processes include an initial grain treatment step wherein the corn kernels are steeped in water, and then separated for processing. In addition to ethanol, wet-milling processes also produce corn gluten feed and corn gluten meal, which are used as animal feed. Dry-milling processes include an initial grain treatment step wherein corn kernels are milled and slurried with water and enzymes to create mash. The mash is then cooked to hydrolyze the starch into glucose sugars which are fermented into ethanol and carbon dioxide. The ethanol is typically further purified via distillation. In addition to ethanol, dry-milling processes produce wet distiller's grains with solubles ("WDGS") and/or dried distiller's grains with solubles ("DDGS"), which may be used as animal feed.

In a dry-milling process, the corn kernels are ground into a corn flour which is referred to as meal. The meal is then slurried with water to form a mash, which is sometimes referred to as a slurry. In some processes, the fibrous materials from the corn flour are separated from the mash and are treated with sulfuric acid ($H_2SO_4$) and enzymes and added back to the slurry in an attempt to increase the ethanol yield. Enzymes, which convert starch to dextrose, as well as ammonia are added to the mash. The ammonia helps control the pH and functions as a nutrient for the yeast, which is added later in the process. The slurry is processed at high temperatures to reduce bacteria levels. Once processed, the slurry is cooled and added to a fermenter where yeast is added to the slurry, and the conversion of sugar to ethanol begins and a beer is formed. During and after fermentation, sulfuric acid ($H_2SO_4$) is added to adjust the pH of the beer. Often the pH of the beer is significantly lowered with the addition of sulfuric acid before distillation of ethanol and formation of whole stillage. After fermentation, corn oil and DDGS are derived from the whole stillage.

As set forth above, in some processes, fibrous materials from the corn flour are separated and are treated with sulfuric acid ($H_2SO_4$) and enzymes in an attempt to increase the ethanol yield and sulfuric acid can also be used to adjust the pH of the beer. However, sulfuric acid has a pKa of about −3 for the first stage of dissociation and a pKa of about +1.9 for the second stage of dissociation. Further, sulfuric acid is a strong sulfonation agent and acts as an oxidizing and/or dehydrating agent.

As such, the strength and corrosivity of sulfuric acid requires certain precautions be taken during its storage, handling, and use in dry-milling processes. Further, it is believed that sulfuric acid contributes to the corrosion of processing equipment which is used in dry-milling processes. Furthermore, sulfuric acid does not readily biodegrade, and, thus, also poses environmental concerns.

With respect to the corn oil and the DDGS which is produced in dry-milling processes, sulfuric acid's strong oxidizing properties, when coupled with the thermal and mechanical stress that is placed on the corn flour and its derivatives during processing, are believed to darken the corn oil and the DDGS produced. In other words, because sulfuric acid is an oxidizing acid, its use coupled with processing high temperatures causes darkening of the non-ethanol products, especially DDGS. From an economic perspective, the color of DDGS is a quality standard which is used to identify DDGS of high nutritional quality. Specifically, DDGS having a homogenous light yellow color is desired.

As such, there remains an opportunity to provide an improved dry-milling process that includes the step of treating the fibrous materials from the corn flour to increase the ethanol yield and that also produces corn oil and DDGS having a homogenous light yellow color.

SUMMARY OF THE INVENTION AND ADVANTAGES

The present disclosure provides a dry-milling process for the production of dried distiller's grains with solubles ("DDGS"). The process includes the steps of dry-milling corn kernels to form a corn flour comprising corn fiber; combining the corn flour with water to form a mash; separating the corn fiber from the mash; treating the separated corn fiber with a composition; combining the treated corn fiber with the mash having the corn fiber separated therefrom to form a slurry; fermenting the slurry to produce beer and carbon dioxide; distilling the beer to produce ethanol and whole stillage; and processing the whole stillage to produce DDGS. The composition includes an alkanesulfonic acid, water, an enzyme, and optionally a surfactant.

The method utilizes the composition to treat corn fiber produced in the dry-milling process which allows for the safe and efficient production of ethanol and DDGS that has optimal color. The alkanesulfonic acid is not as corrosive as acids traditionally used in dry-milling ethanol processes, such as sulfuric acid. Further, the alkanesulfonic acid is readily biodegradable and is, thus, environmentally friendly.

BRIEF DESCRIPTION OF THE DRAWINGS

Other advantages of the present invention will be readily appreciated, as the same becomes better understood by reference to the following detailed description when considered in connection with the accompanying drawings.

DETAILED DESCRIPTION OF THE INVENTION

The present disclosure generally provides an ethanol production process ("the process") comprising the steps of: milling corn kernels to form a corn flour comprising corn fiber; combining the corn flour with water to form a mash; separating the corn fiber from the mash; treating the separated corn fiber with a composition; combining the treated corn fiber with the mash having the corn fiber separated therefrom to form a slurry; fermenting the slurry to produce beer and carbon dioxide; distilling the beer to produce ethanol and whole stillage; and processing the whole stillage to produce dried distiller's grains with solubles ("DDGS").

The composition includes an alkanesulfonic acid, water, an enzyme, and optionally a surfactant.

In various embodiments, the process includes the steps of dry-milling corn kernels to form a corn flour comprising corn fiber; combining the corn flour with water to form a mash; separating the corn fiber from the mash; treating the separated corn fiber with a composition; combining the treated corn fiber with the mash having the corn fiber separated therefrom to form a slurry; fermenting the slurry to produce beer and carbon dioxide; distilling the beer to produce ethanol and whole stillage; and processing the whole stillage to produce DDGS. In this embodiment, the composition includes an alkanesulfonic acid, water, an enzyme, and optionally a surfactant.

In another embodiment, the process includes the steps of dry-milling corn kernels to form the corn flour comprising corn fiber, combining the corn flour with water to form the mash, separating the corn fiber from the mash with a mechanical processor, treating the separated corn fiber with the composition comprising alkanesulfonic acid, water, an enzyme, and optionally a surfactant, combining the treated corn fiber with the mash having the corn fiber separated therefrom to form the slurry, and processing the slurry to produce ethanol and DDGS having a Hunter L* color score of greater than 40, greater than 45, greater than 50, greater than 55, or greater than 60.

In yet another embodiment, the process includes the steps of dry-milling corn kernels to form the corn flour comprising corn fiber, combining the corn flour with water to form the mash, separating corn fiber from the mash, treating the separated corn fiber with a composition, combining the treated corn fiber with the mash having the corn fiber separated therefrom to form the slurry, fermenting the slurry to produce beer and carbon dioxide, distilling the beer to produce ethanol and whole stillage, centrifuging the whole stillage to produce wet cake and thin stillage, evaporating water from the thin stillage to form a syrup, extracting corn oil from the syrup, combining the wet cake and the syrup having the corn oil extracted therefrom to form wet distiller's grains with solubles ("WDGS"), drying the WDGS to produce the DDGS. In this embodiment, the composition includes an alkanesulfonic acid, water, an enzyme, and optionally a surfactant.

The process can be a wet-milling process or a dry-milling process. In various embodiments, the process is a wet-milling (wet-grind) process including an initial grain treatment step wherein the corn kernels are steeped in water, and then separated for processing. In other embodiments, the ethanol process is a dry-milling (dry-grind) process including an initial grain treatment step of grinding corn kernels to form a corn flour.

In many embodiments, the step of grinding the corn kernels is further defined as milling the kernels into coarse flour. The course flour includes corn fiber. In many embodiments, the milled kernels are passed through a fine mesh screen to yield the corn flour. The step of grinding the corn kernels can vary in time because the flour yielded should have a particle size that provides enough surface area to make starch granules available for reaction with water and enzymes and also leaves enough flour to produce WDGS that can be dried to produce DDGS.

In many embodiments, the step of combining the corn flour with water and the enzyme to form the mash (which can also be referred to as the slurry) is further defined as mixing the corn flour yielded in the step of grinding in a slurry mixer with hot water and enzyme such as alpha-amylase in a slurry tank. In some embodiments, only a portion of the enzyme (e.g. alpha-amylase) is added to the slurry tank, and the remaining enzyme is added later in the liquefaction tank. In various embodiments, the step of combining the corn flour with water and the enzyme to form the slurry is conducted at a temperature of from about 60 to about 88° C.

Enzymes can be used in various steps of various embodiments of the process. For example, in some embodiments, one or more enzymes may be added either before, during, or after fermentation to provide benefits such as increases in space-time yield, total product yield, or reduce total energy usage. A wide array of enzyme classes can be utilized. For example, acid cellulases, acid proteases, alpha amylases, beta glucanases, glucoamylases, xylanases, phytases, and/or xylanases enzymes can be utilized. Enzymes of these classes are commercially available under the following trade names: SZM™_XC-150, DELTAZYM® APS acid protease, FERMGEN®, FERMGEN® 2.5X, SZM™ AP-1, FUELZYME®, AVANTEC®, AVANTEC® Amp, LIQUOZYME® SCDS, LIQUOZYME® LpH, SPEZYME® RSL, SPEZYME® CL, SPEZYME CL WB, SPEZYME® Alpha, SPEZYME® Alpha PF, SZM XT-20, STARGEN® 002, STARGEN® 002 WB, OPTIMASH™ TBG, OPTIMASH™ BG, DELTAZYM® GA L-E5 glucoamylase, SPIRIZYME® Excel Plus, DISTALLASE® XP, DISTALLASE® CS, DISTILLASE® CS WB, DISTILLASE® SSF, DISTILLASE® SSF+, GLUCOAMYL™ L 209, GLUCOAMYL™ L-209+, GLUCOAMYL™ L-561, SPIRIZYME® Ultra XHS, SPIRIZYME® Achieve, FUELTASE™, OMPTIMASH™, XYLATHIN®, and OPTIMASH™ VR, and available from BASF, CTE Global, DuPont, Novozymes, and other suppliers.

In some such embodiments of the process, enzymes (e.g. alpha amylase, glucoamylase, acid protease, etc.) can be added to, or present in, the process stream in an amount of from about 0.001 to about 0.2, alternatively from about 0.01 to about 0.1, wt. % based on a total weight of the corn.

Various embodiments of the process include the steps of grinding corn kernels to form a corn flour; combining the corn flour with water and an optionally an enzyme to form a mash; and heating the mash to reduce the viscosity of the mash and form the slurry.

The process stream (e.g. the mash, the slurry) goes through the step of liquefaction, i.e., the step of heating the mash or slurry in the liquefaction tank. Liquefaction occurs at a temperature of from about 84 to about 88° C. During liquefaction, a chemical reaction occurs wherein long starch molecules are broken down into shorter dextrin molecules. Once the process stream, i.e., mash or the slurry, undergoes liquefaction, it is sometimes referred to as a liquefact. Prior to or after liquefaction, the process stream can be ran through a hydro tube, a cook tube, and/or a flash tank.

Notably, the process stream changes as the process progresses and reference to the mash, the slurry, the liquefact, the beer, etc. are used to represent the process stream which is dynamic. For example, the mash can include different components during the various steps of the process but still be referred to as the mash. As another example, the mash can be referred to as the slurry, or the slurry as the liquefact during various steps of the process. In other words, the words mash, slurry, and liquefact, can be used interchangeable in the embodiments of the process disclosed herein.

The process includes the steps of separating corn fiber from the mash, the slurry, or the liquefact, treating the corn fiber with a composition, and combining the treated corn fiber with the mash, the slurry, or the liquefact having the corn fiber separated therefrom to form the slurry. In various alternative embodiments, the step of combining the treated corn fiber with the slurry can be replaced with the step of recombining the treated corn fiber to the process steam during a step of liquefaction (the step of liquefaction is described below) or recombining the treated corn fiber during a step of fermentation (the step of fermentation is described below).

In other alternative embodiments, the treated corn fiber is not reintroduced into the process. In some such embodiments, the treated corn fiber can be processed further and used as animal feed.

In still other alternative embodiments, the treated corn fiber can be fermented to produce ethanol and either reintroduced into the process stream, or be processed further to be used as, for example, animal feed.

In some embodiments, the corn fiber is typically treated with a composition comprising (a)alkanesulfonic acid, (b) an enzyme, (c) water, and (d) optionally a surfactant. If the process includes these additional steps, the alkanesulfonic acid is described further below. In a preferred embodiment, the alkanesulfonic acid is methanesulfonic acid ("MSA"). In embodiments where a surfactant is used, the surfactant can be selected from the group of polyalkyleneoxide, alkylpolyalkyleneoxide, polyoxyethylene sorbitan monolaurate, alkylpolyglycosides, anionic derivatives of alkylpolyglycosides, fatty alcohols, anionic derivatives of fatty alcohols, and phosphate esters. In various embodiments, the step of treating the separated corn fiber with the composition is conducted at a temperature of from about 80 to about 220° C. and at a pressure of from about 40 to about 2600 kPa, at a temperature of from about 80 to about 220° C. and at a pressure of from about 40 to about 4000 kPa, alternatively from about 100 to about 200° C. and at a pressure of from about 100 to about 2000 kPa, alternatively from about 120 to about 180° C. and at a pressure of from about 200 to about 1200 kPa, alternatively from about 140 to about 160° C. and at a pressure of from about 500 to about 800 kPa. In such embodiments, the pressure is typically selected so that at least a part of the water is in the liquid state. In some embodiments, the step of treating the separated corn fiber with the first composition is maintained for a duration of less than about 120 minutes, alternatively less than about 60 minutes, alternatively less than about 30 minutes. In some embodiments, the step of separating the corn fiber from the slurry is conducted with a solids mechanical processor comprising a dynamic filtration device.

When the process includes the additional steps of separating corn fiber from the slurry, treating the corn fiber with a composition, and combining the treated corn fiber with the slurry, the composition utilized comprises the alkanesulfonic acid and the enzyme, or the alkanesulfonic acid and the enzyme are utilized. Of course, one or more (e.g. a combination of) enzymes can be utilized during these additional steps.

In some embodiments, the corn fiber is treated with the alkanesulfonic acid and alpha amylase. The alpha amylase can be added and/or can be present during treatment in an amount of from about 0.005 to about 0.1, alternatively from about 0.01 to about 0.05, wt. % based on a total weight of the corn. In other embodiments, the corn fiber is treated with the alkanesulfonic acid and glucoamylase. The glucoamylase can be added and/or can be present during treatment in an amount of from about 0.01 to about 0.2, alternatively from about 0.03 to about 0.10, wt. % based on a total weight of the corn. In still other embodiments, the corn fiber is treated with the alkanesulfonic acid and acid protease. The acid protease can be added and/or can be present during treatment in an amount of from about 0.001 to about 0.1, alternatively from about 0.002 to about 0.006, wt. % based on a total weight of the corn.

The steps of separating corn fiber from the slurry, treating the corn fiber with a composition, and combining the treated corn fiber with the slurry can be conducted in accordance with Gen 1.5 technology from ICM, Inc. of Colwich, Kans., with the caveat that an alkanesulfonic acid is advantageously used in lieu of sulfuric acid. In such embodiments, the corn fiber is typically separated from protein which can increase the yield of ethanol.

In some embodiments, the process includes the steps of separating solids from a processing stream comprising corn flour separating corn fiber on a mechanical processor, treating the separated corn fiber with a composition comprising alkanesulfonic acid, an enzyme, optionally a surfactant, and water, and reintroducing the treated corn fiber back into the process which yields ethanol and DDGS having a Hunter L* color score of greater than 40, greater than 45, greater than 50, greater than 55, or greater than 60. In such embodiments, all other steps disclosed in the subject disclosure are optional.

In some embodiments, the process includes the steps of separating solids from a processing stream comprising corn flour separating corn fiber on a mechanical processor, treating the separated corn fiber with a composition comprising alkanesulfonic acid, an enzyme, optionally a surfactant, and water, distilling the corn fiber to produce ethanol, and reintroducing the treated corn fiber back into the process stream or utilizing the treated corn fiber otherwise.

The composition can be supplied as a single component or in multiple components. In some embodiments, the composition is supplied in two or more discreet components, which can be blended together prior to use. For example, the mixture can be supplied in a two component (2K) system, with one component comprising the alkanesulfonic acid, and the other component comprising the surfactant, water, and other additives. In this example, the two components can be provided separately and blended together on site at the location of use prior to use and, if desired, diluted with water. In another embodiment, a single component composition can be provided as a concentrate, and diluted on site prior to use.

The composition comprises the alkanesulfonic acid. The alkanesulfonic acid is particularly useful for replacing conventional acids, e.g. sulfuric acid. Of course, one or more different alkanesulfonic acids can be used to treat the corn fiber. Further, the alkanesulfonic acid may be used to treat the corn fiber alone or mixed with one or more additional components, such as water, other acids, surfactants, etc. In certain embodiments, the alkanesulfonic acid is mixed with water. If the alkanesulfonic acid is mixed with water, the alkanesulfonic acid can be mixed with the water in different amounts. In other words, composition comprising the alkanesulfonic acid can be used to treat the corn fiber at different concentrations.

The alkanesulfonic acid can be a short chain alkanesulfonic acid, such as one containing from 1 to 4 carbon atoms (e.g. one having propyl, ethyl, or methyl moieties). Typically, the alkanesulfonic acid is methanesulfonic acid ("MSA"). MSA is a strong organic acid that is believed to be completely non-oxidizing and thermally stable that forms highly soluble salts. In addition, MSA has a low vapor pressure, has no odor, and is biodegradable. As such, MSA is easy to handle and use and environmentally friendly, especially in comparison to other strong acids known in the art such as sulfuric acid, nitric acid, and hydrochloric acid.

In a preferred embodiment, the alkanesulfonic acid comprises or is the MSA. MSA is soluble in water and has a pKa of −1.9, which is about the pKa of the first stage of dissociation sulfuric acid (−3 for the first stage of dissociation, 1.9 for the second stage of dissociation). MSA has a lower corrosivity in comparison to sulfuric acid, nitric acid, hydrochloric acid, and does not act as an oxidizing and/or dehydrating agent. Further, MSA, unlike sulfuric acid, is not a sulfonation agent. To this end, it is believed that use of MSA minimizes the corrosion of processing equipment and the degradation of organic matter when used in the process.

In various embodiments, the alkanesulfonic acid (e.g. MSA) can be used with one or more additional acids. For example, in various embodiments, the one or more additional acids selected from hydrochloric acid, nitric, sulfuric acid, phosphoric acid, formic acid, and combinations thereof. In one embodiment, a composition comprising MSA, phosphoric acid, and water are used. In another embodiment, MSA, formic acid, and water are used. In yet another embodiment, MSA, sulfuric acid, and water are used. In some embodiments, the step of treating the corn fiber is substantially free of or free of additional acids, e.g. sulfuric acid. The terminology "substantially free", as used herein in reference to these acids, refers to a sufficiently low amount of these acids. Typically, the amount of other acids is less than about 5, alternatively less than about 4, alternatively less than about 3, alternatively less than about 2, alternatively less than about 1, alternatively less than about 0.5, and alternatively less than about 0.3, parts by weight based on 100 parts by weight, based on the total weight of acid used to treat the corn fiber.

In some embodiments, the alkanesulfonic acid is present in the composition in an amount of from about 0.1 to about 15, alternatively from about 0.1 to about 5, alternatively from about 0.2 to about 4, alternatively from about 0.4 to about 2, parts by weight based on 100 parts by weight of the composition. The amount of the alkanesulfonic acid present in the composition may vary outside of the ranges above, but is typically both whole and fractional values within these ranges. Further, it is to be appreciated that more than one type of alkanesulfonic acid may be included in the composition, in which case the total amount of the alkanesulfonic acid is within the above ranges.

Alternatively, the alkanesulfonic acid can be utilized in a corn to alkanesulfonic acid weight ratio from 1:1.78 to 3000:1.

The composition comprises water. That is, the alkanesulfonic acid is aqueous. If the alkanesulfonic acid is aqueous, the alkanesulfonic acid, e.g. MSA, is typically present in an amount of from about 35 to about 95, alternatively from about 50 to about 85, alternatively from about 65 to about 85, alternatively about 70, alternatively greater than about 99 parts by weight, each based on the combined weight of the alkanesulfonic acid and water.

Non-limiting examples of suitable alkanesulfonic acids, for purposes of the present disclosure, are commercially available from BASF Corporation of Florham Park, N.J., under the trade name LUTROPUR®, such as LUTROPUR® M, LUTROPUR® MSA, and LUTROPUR® MSA 100. In certain embodiments, the MSA is one which is formed by an air oxidation process, rather than from a chlorooxidation process. As such, the MSA has less metal content, such as less than about 1 mg/kg, and little to no chloro compounds, which are generally corrosive. Other non-limiting examples of suitable alkanesulfonic acids are described in U.S. Pat. No. 6,531,629 to Eiermann et al. and in U.S. Pat. App. Pub. No. 2008/0161591 to Richards, the disclosures of which are incorporated herein by reference in their entirety to the extent they do not conflict with the general scope of the present disclosure.

The composition optionally includes an enzyme such as those described above. In some embodiments where an enzyme is used, the enzyme is selected from an acid cellulase, an acid protease, an alpha amylase, a beta glucanase, a glucoamylase, a xylanase, and combinations thereof. In certain embodiments the enzyme and the alkanesulfonic acid (e.g. MSA) are present in the composition in a weight ratio of from about 1:1000 to about 1:50, alternatively from about 1:800 to about 1:100.

In various embodiments, one or more enzymes selected from the group consisting of beta-glucosidases, exo-cellobiohydrolases, endo- and exo-glucanases, glucoside hydrolases, and xylanases are included in the composition. Yeast can also be included in the composition.

The composition optionally includes a surfactant. If employed, the surfactant is typically selected from the group of nonionic surfactants, anionic surfactants, and ionic surfactants. It is to be appreciated that other types of surfactants can also be used.

In various embodiments, the surfactant comprises a non-ionic surfactant, or is a non-ionic surfactant. When used in conjunction with the alkanesulfonic acid, it is believed that the non-ionic surfactant helps accelerate the degradation or breakdown of fiber by facilitating the wet-out of the fiber with the methanesulfonic acid.

Non-ionic surfactants, suitable for purposes of the present disclosure, include alcohol alkoxylates. Suitable alcohol alkoxylates include linear alcohol ethoxylates. Additional alcohol alkoxylates include alkylphenol ethoxylates, branched alcohol ethoxylates, secondary alcohol ethoxylates, castor oil ethoxylates, alkylamine ethoxylates (also known as alkoxylated alkyl amines), tallow amine ethoxylates, fatty acid ethoxylates, sorbital oleate ethoxylates, end-capped ethoxylates, or combinations thereof. Further non-ionic surfactants include amides such as fatty alkanolamides, alkyldiethanolamides, coconut diethanolamide, lauramide diethanolamide, cocoamide diethanolamide, polyethylene glycol cocoamide, oleic diethanolamide, or combinations thereof. Yet further non-ionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl polyglycocides, or combinations thereof.

Non-ionic surfactants, also suitable for purposes of the present disclosure, include polyalkylene oxide surfactants (also known as polyoxyalkylene surfactants or polyalkylene glycol surfactants). One such example of a suitable surfactant is described as a natural oil polyol herein. Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block and random copolymers. These surfactants generally comprise a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. The surfactant may also include butylene oxide (BO) blocks, and can include random incorporations of two or three alkylene oxides, e.g.

EO/PO/BO, EO/PO/PO, EO/EO/PO, etc. Such surfactants may be referred to in the art as "heteric" block surfactants. Suitable surfactants of this type also include random EO, PO, and/or BO co- and ter-polymers.

In many embodiments, the composition comprises a surfactant selected from the group of polyalkyleneoxides, alkylpolyalkyleneoxides, polyoxyethylene sorbitan monolaurates, alkylpolyglycosides, anionic derivatives of alkylpolyglycosides, fatty alcohols, anionic derivatives of fatty alcohols, and phosphate esters.

In one embodiment, the alkanesulfonic acid is used with the surfactant comprising one or more compounds selected from the group consisting of compounds of formula (I):

(I)

and surfactants which are not compounds of formula (I), wherein in formula (I):

$R^1$ and $R^2$ are independently selected from the group consisting of hydrogen, unsubstituted and substituted alkyl with 1 to 22 carbon atoms, and unsubstituted and substituted aryl, wherein in the substituted alkyl and the substituted aryl each substituent is independently selected from the group consisting of —$OSO_3H$, —$SO_3H$, —COOH and —$OPO_3H_2$ and salts thereof;

each $R^x$ is independently selected from the group consisting of hydrogen and alkyl with 1 to 20 carbon atoms; and X is an integer from about 1 to about 2400, alternatively from about 4 to about 1000, alternatively form 8 to 300.

Other non-limiting examples of suitable surfactants that can be used in combination with the alkanesulfonic acids are described in WO 2015/049345 to Rittig et al., the disclosure of which is incorporated herein by reference in its entirety to the extent that it does not conflict with the general scope of the present disclosure.

Non-limiting examples of suitable non-ionic surfactants, for purposes of the present disclosure, are commercially available from BASF Corporation, under the trade names of PLURAFAC®, PLURONIC®, TETRONIC®, LUTROPUR®, and LUTENSOL®.

As alluded to above, it is believed that use of the surfactant in combination with the alkanesulfonic acid provides a synergistic effect on the process in some embodiments. Typically, the ratio of the alkanesulfonic acid to the surfactant, by weight, in the composition is from about 120:1 to about 1:4, alternatively from about 20:1 to about 1:2, alternatively from about 10:1 to about 1:1, alternatively from about 5:1 to about 2:1.

As is alluded to above the step of treating the separated corn fiber with a composition can occur in various sequences of steps of various times. For example, the corn fiber can be treated with a single composition comprising alkanesulfonic acid, optionally a surfactant, water, and an enzyme. As another example, the corn fiber can be treated with a composition comprising alkanesulfonic acid, optionally a surfactant, water for a given period of time, e.g. 30 minutes, and then the enzyme, can be added to the composition and the treated the corn fiber can be exposed to the composition, now including enzyme, for another period of time, e.g. 30 minutes.

As is alluded to above, in various embodiments, the process can include the step of adding a defoamer. The process can include any defoamer known in the art. Of course, the process can include more than one defoamer, i.e., a combination of different defoamers. Examples of suitable defoamers include silicone based defoamers and non-ionic block copolymers.

In various embodiments, the composition can include a corrosion inhibitor. The corrosion inhibitor may be defined, in general terms, as a substance that, when added, reduces the corrosion rate of a metal exposed to the various materials of the ethanol process. To this end, the corrosion inhibitor is useful for inhibiting corrosion of the surface of the equipment used in the process. Any corrosion inhibitor known in the art can be used. Of course, the composition can include more than one corrosion inhibitor, i.e., a combination of different corrosion inhibitors.

In one embodiment, the corrosion inhibitor comprises an amphoteric surfactant. As such, the corrosion inhibitor may be the amphoteric surfactant or may include one or more additional components, such as water. If the corrosion inhibitor includes water, the amphoteric surfactant can be provided in various concentrations. Suitable amphoteric surfactants, for purposes of the present disclosure, include betaines, imidazolines, and propionates. Further examples of suitable amphoteric surfactants include sultaines, amphopropionates, amphrodipropionates, aminopropionates, aminodipropionates, amphoacetates, amphodiacetates, and amphohydroxypropylsulfonates. In certain embodiments, the amphoteric surfactant is at least one of a propionate or an amphodiacetate. Further specific examples of suitable amphoteric surfactants include N-acylamino acids such as N-alkylaminoacetates and disodium cocoamphodiacetate, and amine oxides such as stearamine oxide. In one embodiment, the amphoteric surfactant comprises disodium cocoamphodiacetate.

In certain embodiments, the amphoteric surfactant is illustrated by the formulas: $RCH_2NHCH_2CH_2COOM$ or $RCH_2N(CH_2CH_2COOM)_2$, wherein M is a salt-forming cation (e.g. Na or H) and R is the hydrocarbon moiety of the long-chain fatty acid RCOOH, e.g. a $C_7$ to $C_{35}$, or a $C_7$ to $C_{18}$, fatty acid. Such amphoteric surfactants include sodium N-coco-β-aminopropionate, N-coco-β amino propionic acid; N-lauryl, myristyl-β-amino propionic acid; disodium N-tallow-β-iminopropionate; disodium N-lauryl-β-iminopropionate (also known as sodium lauriminodipropionate); and the partial sodium salt of N-lauryl-β-iminopropionic acid. In one embodiment, the amphoteric surfactant comprises sodium lauriminodipropionate.

As alluded to above, in certain embodiments, the corrosion inhibitor is aqueous. If the corrosion inhibitor is aqueous, the amphoteric surfactant is typically present in an amount of from about 15 to about 95, or about 20 to about 80, or about 25 to about 60, or about 30 to about 50, parts by weight, each based on 100 parts by weight of the corrosion inhibitor.

Water can be utilized with the alkanesulfonic acid and, if included, the surfactant. That is, in many embodiments, the alkanesulfonic acid is diluted, i.e., aqueous. The water can be of various types. In certain embodiments, the water is de-mineralized and/or de-ionized. The water is present in the composition in various amounts, depending on the embodiment. The water can be added to the composition as a separate component. However, it is to be appreciated that some of the water can also be imparted by the components of the composition, such as by the alkanesulfonic acid (when aqueous), the defoamer (when aqueous), etc.

The composition can further include one or more additives. Various types of additives can be used. Examples of suitable additives include colorants, antioxidants, dispersants, stabilizers, viscosity modifiers, and combinations thereof.

Some embodiments include the additional step of separating corn oil from the mash, slurry, liquefact, at any point in the process stream. Generally, corn fiber (solids) are separated from the process stream, and corn oil is then extracted from the process stream. In some such embodiments, the corn fiber is treated with the composition, and corn oil is also extracted from the treated corn fiber. In some such embodiments, the corn oil is separated during mechanical processing. In some embodiments the corn fiber is fermented.

In some such embodiments, the step of separating corn oil from the mash/slurry is further described as a "front end" oil extraction step or sub process. In some embodiments, the "front end" oil extraction process extracts corn oil from the mash, slurry, or liquefact (all three of which can be used interchangeably in the steps described below). Various embodiments of the front end oil extraction process optionally include the step of wet-milling the mash. The front end oil extraction process includes the step of processing/separating the mash to produce a light phase and a heavy phase. The step of separating can be conducted on a centrifuge, a paddle screen, or any other separation apparatus known in the art. In some embodiments, the step of separating the mash to produce a light phase and a heavy phase is further defined as separating the mash to produce a light phase and a heavy phase via centrifugation. In some embodiments, the step of separating the mash to produce a light phase and a heavy phase is further defined as separating the mash to produce a light phase and a heavy phase via a first centrifugation, and via a second, subsequent, centrifugation.

In some embodiments, the step of extracting corn oil from the mash further comprises the sub step of fermenting the heavy phase, the light phase, or any combination thereof to produce alcohol.

Some embodiments of the process that include the "front end" oil extraction steps, further include the step of adding the alkanesulfonic acid and/or the enzyme to the heavy phase, the light phase, or any combination thereof. Of course, one or more (e.g. a combination of) enzymes can be utilized during these additional steps. Of course, one or more (e.g. a combination of) enzymes can be utilized. In some embodiments of the front end oil extraction process, the heavy phase, the light phase, or any combination thereof is treated with the alkanesulfonic acid and alpha amylase. The alpha amylase can be added and/or can be present during treatment in an amount of from about 0.005 to about 0.1, alternatively from about 0.01 to about 0.05, wt. % based on a total weight of the corn. In other embodiments of the front end oil extraction process, the heavy phase, the light phase, or any combination thereof is treated with the alkanesulfonic acid and glucoamylase. The glucoamylase can be added and/or can be present during treatment in an amount of from about 0.03 to about 0.10, alternatively from about 0.01 to about 0.20, wt. % based on a total weight of the corn. In still other embodiments of the front end oil extraction process, the heavy phase, the light phase, or any combination thereof is treated with the alkanesulfonic acid and acid protease. The acid protease can be added and/or can be present during treatment in an amount of from about 0.001 to about 0.1, alternatively from about 0.002 to about 0.006, wt. % based on a total weight of the corn.

Alkanesulfonic acid is added to the light phase and corn oil is then extracted, e.g. via centrifugation. In some embodiments, the alkanesulfonic acid and optionally the enzyme is added to the light phase in an amount sufficient to adjust pH to a range of from about 2 to about 5, alternatively from about 3 to about 5, alternatively from about 3.5 to about 4.5. Alternatively, in some embodiments, the alkanesulfonic acid is added to the light phase in an amount of from about 0.05 to about 2, alternatively from about 0.1 to about 1, parts by weight based on 100 parts by weight of the light phase. In some embodiments, sulfuric acid is also used to treat the light phase. In other embodiments, the front end oil extraction step or sub process utilizes an alkanesulfonic acid and is free of any other additional acid(s). In many embodiments, the alkanesulfonic acid is MSA. In some embodiments, the step of extracting corn oil from the thin component is conducted in the presence of alpha-amylase.

In some embodiments, once the alkanesulfonic acid is added to the light phase and the mixture is aged in a holding tank for a period of from about 0.5 to about 5, alternatively from about 0.5 to about 2, alternatively from about 0.5 to about 1.5, hours prior to oil extraction. In some embodiments, the mixture is agitated during aging, e.g. mechanically agitated with a blade, agitated via fluid movement with a pump, etc.

After oil extraction, the light phase, having the oil extracted therefrom, and the heavy phase are recombined to form the mash which can be reintroduced to the process stream (typically prior to the step of distilling) of the dry milling process and continue through any combination of the steps disclosed.

In many embodiments, after formation of the slurry in the slurry tank, the slurry then typically enters a cooker (e.g. a cook tube) and is heated to a temperature greater than about 220° F. in the cooker/steamer. Once heated, the slurry is typically cooled by a sudden drop in pressure in a vessel (e.g. a flash tank, a cooling column, etc.) for a time of from about 1 to about 30, alternatively from about 2 to about 15, minutes. Once cooled, the slurry typically enters a liquefaction tank where an additional enzyme (e.g. alpha-amylase and/or any of the enzymes described above) is added to the slurry (sometimes referred to as mash) and the slurry is allowed to further chemically react (i.e. liquefy) for a time of from about 10 to about 60, alternatively about 30, minutes. In some embodiments, liquefaction, i.e., the step of heating the slurry in the liquefaction tank, occurs at a temperature of from about 84 to about 88° C. The chemical reaction which is referred to can be described as the breaking down of long starch molecules into shorter dextrin molecules.

The process also includes the step of fermenting the slurry thereby producing beer and carbon dioxide. The slurry enters a fermentation tank(s) where additional enzymes are added (e.g. glucoamylase). In some embodiments, the step of fermenting is conducted at a temperature of from about 15 to about 50, alternatively from about 17 to about 33, alternatively from about 30.5 to about 34.4, ° C.

During fermentation, glucose is typically converted with yeast as it moves through a series of multi-step reactions to ethanol and carbon dioxide in the fermentation tank. Yeast can withstand extreme environmental stresses including high temperatures, a lower pH, high ethanol concentrations, and organic acids produced by contaminating bacteria. That is, yeast is a robust microscopic fungus which is capable of converting sugar into alcohol and carbon dioxide in a wide variety of conditions. Fortunately, most bacterial contaminants do not grow below pH 4. Bacterial contaminants (e.g. microorganisms) can lower ethanol yield by converting glucose to undesirable fermentation products such as fusel oils, acetic acid, and lactic acid. In various embodiments, antibiotics may be added during the step of fermenting to minimize bacterial contamination.

In some embodiments, the process utilizes simultaneous saccharification and fermentation, a saccharifying enzyme (e.g. glucoamylase) is added directly to the fermentation tank.

In many embodiments, fermentation is conducted in the presence of the enzyme. Of course, one or more (e.g. a combination of) enzymes can be utilized. In many such embodiments, an enzyme (e.g. alpha amylase, glucoamylase, acid protease, etc.) can be added to, or present in, the process stream for fermentation and the alkanesulfonic acid (e.g. MSA) can be added to the process stream for distillation. In some embodiments, both the alkanesulfonic acid and the enzyme are added to the process stream for fermentation.

For example, in some embodiments, fermentation is conducted in the presence of alpha amylase. The alpha amylase is added and/or is present during fermentation in an amount of from about 0.005 to about 0.1, alternatively from about 0.01 to about 0.05, wt. % based on a total weight of the corn.

For example, in other embodiments, fermentation is conducted in the presence of glucoamylase. The glucoamylase is added and/or is present during fermentation in an amount of from about 0.01 to about 0.20, alternatively from about 0.03 to about 0.10, wt. % based on a total weight of the corn.

As another example, in some embodiments, fermentation is conducted in the presence of acid protease. The acid protease is added and/or is present during fermentation in an amount of from about 0.001 to about 0.1, alternatively from about 0.002 to about 0.006, wt. % based on a total weight of the corn. At the end of fermentation, the product is called beer and typically includes greater than 12% by weight ethanol.

In one embodiment, the step of fermenting the slurry to form the beer is conducted in the presence of phytase, and an alkanesulfonic acid, e.g. MSA, is subsequently added to the beer. In some such embodiments, the phytase and the alkanesulfonic acid are added in a weight ratio of from about 1:1000 to about 1:50, alternatively from about 1:500 to about 1:50, alternatively from about 1:400 to about 1:70.

The process optionally includes the step of adding the alkanesulfonic acid to the beer in an amount sufficient to adjust the pH to a range of from about 3 to about 6.5, alternatively from about 3 to about 5.5, alternatively from about 3.5 to about 5, alternatively from about 4 to about 5, alternatively about 4.5, alternatively from about 5.5 to about 6, alternatively about 5.8. In various embodiments, the alkanesulfonic acid is added to the beer in an amount of from about 0.05 to about 3, alternatively from 0.05 to about 2, alternatively from 0.1 to about 1, alternatively from about 0.2 to about 0.8, alternatively from about 0.3 to about 0.6, alternatively from about 0.4 to about 0.5, parts by weight based on 100 parts by weight of the beer. In some embodiments, the step of adding an alkanesulfonic acid to the beer is conducted prior to and/or during the step of fermenting.

The alkanesulfonic acid can be added to the beer all at once or in multiple increments. That is, alkanesulfonic acid can be added to the beer in a single addition or over multiple additions (e.g. 2, 3, 4, 5, 6, 7, 8, 9, and so on and so forth). If the process is continuous, the alkanesulfonic acid can be added in a continuous manner, e.g. a continuous flow or incrementally over time. The alkanesulfonic acid is just as previously described.

The alkanesulfonic acid can be supplied as is or in a mixture. If the alkanesulfonic acid is supplied in a mixture, it can be supplied in two or more discreet components, which can be blended together prior to use. For example, the mixture can be supplied in a two component (2K) system, with one component comprising the alkanesulfonic acid, and the other component comprising the surfactant, water, and other additives.

In various embodiments, the alkanesulfonic acid (e.g. MSA) can be used with one or more additional acids. For example, in various embodiments, the one or more additional acids selected from hydrochloric acid, nitric, sulfuric acid, phosphoric acid, formic acid, and combinations thereof. In one embodiment, MSA, phosphoric acid, and water are used. In another embodiment, MSA, formic acid, and water are used. In yet another embodiment, MSA, sulfuric acid, and water are used; i.e. sulfuric acid is present during the step of adding an alkanesulfonic acid to the beer in an amount sufficient to adjust the pH to a range of from about 3 to about 5.5. In some embodiments, the step of an alkanesulfonic acid to the beer in an amount sufficient to adjust the pH to a range of from about 3 to about 5.5 is free of sulfuric acid. In other embodiments, the step of adding an alkanesulfonic acid to the beer in an amount sufficient to adjust the pH to a range of from about 3 to about 5.5 is free of any other additional acid.

In embodiments where the alkanesulfonic acid (e.g. MSA) is used with an additional acid, the step of acidifying the beer includes the use of an alkanesulfonic acid and the additional acid of acids in a total amount sufficient to adjust the pH to a range of from about 3 to about 6.5, alternatively from about 3 to about 5.5, alternatively from about 3.5 to about 5, alternatively from about 4 to about 5, alternatively about 4.5, alternatively from about 5.5 to about 6, alternatively about 5.8. In various embodiments, the alkanesulfonic acid is added in combination with sulfuric acid in any ratio to achieve the desired pH. In some embodiments, the step of adding an alkanesulfonic acid and other acid to the beer is conducted prior to and/or during the step of fermenting.

In one embodiment, the step of adding an alkanesulfonic acid to the beer in an amount sufficient to adjust the pH to a range of from about 3 to about 5.5 is substantially free to completely free of phosphoric acid. In another embodiment, the step of adding an alkanesulfonic acid to the beer in an amount sufficient to adjust the pH to a range of from about 3 to about 5.5 is substantially free to completely free of nitric acid. In yet another embodiment, the step of adding an alkanesulfonic acid to the beer in an amount sufficient to adjust the pH to a range of from about 3 to about 5.5 is substantially free to completely free of sulfuric acid. These embodiments are effective allow for quick pH adjustment, provide improved ease of handling, provide optimal output (of ethanol and corn oil and DDGS having lighter color), and are environmentally friendly. However, in some embodiments, the step of adding an alkanesulfonic acid to the beer in an amount sufficient to adjust the pH to a range of from about 3 to about 5.5 can also comprise the alkanesulfonic acid (e.g. MSA) and one of, or any combination of, other acids.

The terminology "substantially free", as used herein in reference to these acids, refers to a sufficiently low amount of these acids. Typically, the amount of other acids is less than about 5, alternatively less than about 4, alternatively less than about 3, alternatively less than about 2, alternatively less than about 1, alternatively less than about 0.5, and alternatively less than about 0.3, parts by weight based on 100 parts by weight, based on the total weight of acid added to the beer to adjust the pH. In many embodiments, the step of adding an alkanesulfonic acid to the beer in an amount sufficient to adjust the pH to a range of from about 3 to about 5.5 is substantially free of additional acids (i.e., acids other than the alkanesulfonic acid).

As alluded to above, in certain embodiments, the alkanesulfonic acid is aqueous. If the alkanesulfonic acid is aqueous, the alkanesulfonic acid, e.g. MSA, is typically present in an amount of from about 35 to about 95, alternatively from about 50 to about 85, alternatively from about 65 to about 85, alternatively about 70, alternatively greater than about 99 parts by weight, each based on the combined weight of the alkanesulfonic acid and water. Further, it is to be appreciated that more than one alkanesulfonic acid may be included in the acidic component, in which case the total amount of all the alkanesulfonic acid included is typically within the above ranges.

The alkanesulfonic acid is particularly useful for replacing conventional acids, e.g. sulfuric acid which has been used to adjust the pH of the beer in ethanol production processes. Of course, one or more different alkanesulfonic acids can be used to adjust the pH of the beer in the process. Further, the alkanesulfonic acid may be used to adjust the pH of the beer in the process alone or mixed with one or more additional components, such as water, other acids, surfactants, etc. In certain embodiments, the alkanesulfonic acid is mixed with water. If the alkanesulfonic acid is mixed with water, the alkanesulfonic acid can be mixed with the water in different amounts. In other words, the alkanesulfonic acid can have different concentrations. The alkanesulfonic acid may be used to adjust the pH of the beer with a surfactant selected from the group of nonionic surfactants, anionic surfactants, and ionic surfactants. It is to be appreciated that other types of surfactants can also be used. The any surfactant described in this disclosure can be used in combination with alkanesulfonic acid to adjust the pH of the beer.

In one embodiment, the step of adding an alkanesulfonic acid to the beer in an amount sufficient to adjust the pH to a range of from about 3 to about 5.5 is further defined as adding the alkanesulfonic acid (e.g. MSA), a surfactant, and water to the beer to adjust the pH to a range of from about 3 to about 5.5. It is contemplated herein that the individual components added can be added in various amounts. For example, a mixture comprising the alkanesulfonic acid (e.g. MSA) and the surfactant with a minimal amount of or even no water, which can be diluted with water prior to use, is contemplated herein.

The process also includes the step of distilling the beer to produce ethanol and whole stillage. In some embodiments, the step of distilling the beer is conducted at a temperature of from about 80 to about 130, alternatively of from about 90 to about 120, ° C.

In many embodiments, the beer is distilled in a distillation system consisting of three columns. In such embodiments, the beer is degassed in a degassing column (a first column). During degassing, carbon dioxide and other gases are removed from the beer. Next, ethanol and water are separated from non-converted solids in a separation column (a second column). The non-converted solids (whole stillage) fall to the bottom and are sent to the centrifuge for separation. The ethanol and water are separated in a rectifier column (a third column). That is, the ethanol is purified in the rectifier column.

In some embodiments, after the step of distilling, the ethanol is further processed in a molecular sieve to convert it to about 200 proof. In many embodiments, the process yields about 190 proof ethanol (about 95% pure ethanol) because ethanol and water form an azeotrope. The remaining about 5% water is removed by molecular sieves during the step of processing in a molecular sieve. Molecular sieves rely on pore sizes to separate the smaller water molecules from ethanol.

As is described above, the solid materials generated during the step of distilling (in the second column during the distillation of ethanol from beer) is called whole stillage. In many embodiments, whole stillage comprises from about 10 to about 20% by weight solids and is composed primarily of small particles of corn that did not get converted to ethanol. The process also includes the step of centrifuging the whole stillage to produce wet cake and thin stillage.

The process includes the step of processing the whole stillage to form DDGS. In many embodiments, the step of processing the whole stillage to form DDGS includes the sub steps of: centrifuging the whole stillage to produce wet cake and thin stillage; evaporating water from the thin stillage to form a syrup; extracting corn oil from the syrup; combining the wet cake and the syrup to form wet distiller's grains with solubles ("WDGS"); and drying WDGS to produce DDGS having a Hunter L* color score of greater than 40.

The wet cake is simply a more concentrated form of the whole stillage and typically includes about 35% by weight solids after leaving the centrifuge. Since the whole stillage includes a significant % by weight solids, in many embodiments the wet cake is augured or conveyed to a drum dryer.

The thin stillage comprises water and, in some embodiments, from about 3 to about 12, alternatively from about 4 to about 5, % by weight solids. In some embodiments, the thin stillage is processed in an evaporator, to yield a syrup. In most embodiments, the syrup comprises from about 25 to about 35, alternatively from about 28 to about 30, % by weight solids and consists essentially of protein and oils from the corn. That is, the process also includes the step of evaporating water from the thin stillage to form the syrup. In some embodiments, the evaporated water is condensed and recycled to the slurry tank. In such embodiments, the condensed water is referred to as backset and helps to conserve total water usage in the process.

The process may also include the step of extracting corn oil from the syrup. In some embodiments, the step of extracting corn oil from the thin stillage is conducted in the presence of methanesulfonic acid. In some embodiments, the step of extracting corn oil from the syrup is conducted in the presence of a surfactant selected from the group of polysorbates, polyglycosides, polyalkylene oxides, and combinations thereof. In some embodiments, the step of extracting corn oil from the syrup is conducted in the presence of a combination of surfactants (e.g. a combination of any of the surfactants described herein).

In a preferred embodiment, alkanesulfonic acid is added to thin stillage prior to the step of evaporating water from the thin stillage to form a syrup. The addition of the alkanesulfonic acid, e.g. MSA, prior to evaporation is believed to reduce fouling in the evaporators.

In some embodiments, the step of extracting corn oil from the syrup is conducted in the presence of a surfactant, e.g. a polyalkylene oxide-containing surfactant or any of the surfactants described herein and nano-$SiO_2$. One such demulsifier is described in "The Application and Research of Dispersing in Situ nano-$SiO_2$ in Polyether Demulsifier TA1031" to Fang-Hui et al. in the Journal of Dispersion Science and Technology 29: 1081-1084, 2008, which is incorporated in its entirety herein.

In some embodiments, the process includes the step of adding a surfactant to a process stream of the process, i.e., the step of adding a surfactant at any point in the process.

Surfactants can be used to increase the quality and/or yield of corn oil, ethanol, DDGS, etc. Any surfactant known in the art and described herein can be added. The surfactant can be added with the alkanesulfonic acid or another component. Alternatively, the surfactant can be added separate from any other components.

In some embodiments, the process includes the step of adding a natural oil polyol to a process stream of the process. The natural oil polyol comprises the reaction product of a natural oil component and an alkylene oxide. The natural oil polyol is different than the other surfactants described herein. The natural oil polyol is added to facilitate the removal of corn oil from the process stream and can be added to the process stream at any point in the corn-to-ethanol process. That is, the natural oil polyol can be added to the mash, to the beer, to the whole stillage, etc., as is described herein. In many embodiments, the natural oil is typically added to the process stream in an amount of from about 2 to about 1,000, alternatively from about 50 to about 500, PPM based on 100 parts by weight of the process stream. When the process includes the step of adding the natural oil polyol to the process stream of the process, the steps of adding the natural oil polyol to a process stream of the process and extracting corn oil can happen at any point in the process. For example, the natural oil can be added to the syrup and the corn oil extracted therefrom. As another example, the natural oil can be added to the mash and the corn oil extracted therefrom.

In many embodiments, the natural oil polyol has a hydroxyl functionality of about 2 or greater, alternatively about 2.5 or greater, alternatively about 3.0, alternatively from about 1.5 to about 3.5, alternatively from about 2.0 to about 3.0. The hydroxyl functionality as used herein is the average number of hydroxyl groups on a molecule and is calculated with the following formula: Average Functionality=Total Moles OH/Total Moles Polyol. As such, the nominal functionality or hydroxyl functionality of the natural oil polyol does not have to be a whole number and is, in many cases, reported as a number including a fraction such as 2.8. The hydroxyl functionality of the natural oil polyol may vary outside of the ranges above, but is typically a whole or fractional value within those ranges.

In many embodiments, the natural oil polyol has a number average molecular weight ($M_n$) of from about 100 to about 3,000, alternatively from about 150 to about 2,500, alternatively from about 150 to about 2,000, alternatively from about 500 to about 2,000, g/mol. Molecular weight as used herein is the number average molecular weight ($M_n$) which is defined as the statistical average molecular weight of all the polymer chains in the sample, and is defined with the formula $M_n = \Sigma N_i M_i / \Sigma N_i$ where $M_i$ is the molecular weight of a chain and $N_i$ is the number of chains of that molecular weight. $M_n$ can be predicted by polymerization mechanisms and is measured by methods that determine the number of molecules in a sample of a given weight; for example, colligative methods such as end-group assay. The $M_n$ of the natural oil polyol may vary outside of the ranges above, but is typically a whole or fractional value within those ranges.

In many embodiments, the natural oil polyol has a hydroxyl value of from about 15 to about 100 mg KOH/g, alternatively from about 20 to about 75, mg KOH/g as calculated using DIN 53240. Hydroxyl value as used herein is the number of milligrams of potassium hydroxide required to neutralize the acetic acid taken up on acetylation of one gram of a chemical substance that contains free hydroxyl groups. The hydroxyl value of the natural oil polyol may vary outside of the ranges above, but is typically a whole or fractional value within those ranges.

In various embodiments, the natural oil polyol has an HLB value of greater than about 8, alternatively greater than about 10, alternatively greater than about 12, alternatively from about 8 to about 20, alternatively from about 10 to about 20, alternatively from about 12 to about 20, alternatively from about 10 to about 15, alternatively from about 12 to about 14. HLB value as used herein is calculated based on William C. Griffin's formula for non-ionic surfactants. William C. Griffin's HLB formula is the percent of total hydrophile divided by 5 to standardize the value against a scale of 20. The percent hydrophile of the natural oil polyol is defined as the total sum of percent EO and the percent of polyhydric alcohols (i.e. glycerol). The HLB of the natural oil polyol may vary outside of the ranges above, but is typically a whole or fractional value within those ranges.

The natural oil polyol comprises the reaction product of a natural oil component and an alkylene oxide. The natural oil component is derived from a natural oil. Typically, the natural oil component is a natural oil or functionalized natural oil. To this end, the natural component is not derived from a sorbitol, a sorbitan, or an isosorbide. The natural oil component is defined as a non-petroleum oil. Generally, the natural oil component includes at least one natural oil and/or a reaction product of at least one natural oil and a compound reactive with the natural oil. The natural oil component is a feedstock formed from the renewable resource such as soy bean oil and/or other renewable resources that can be generated by means such as harvesting plant crops. Use of feedstocks formed from renewable resources reduces environmental impact by decreasing demand on petroleum oils and other non-renewable resources.

The natural oil component is typically hydroxyl functional. Hydroxyl functionality provides one or more reaction sites on the natural oil component at which polymeric side chains can bond.

Typically, the natural oil component comprises a natural oil. One particularly suitable natural oil is castor oil. Castor oil comprises triglycerides. A triglyceride is a glyceride in which glycerol is esterified with three fatty acids, i.e., castor oil comprises triglycerides, which comprise fatty acids. Approximately 90% of these fatty acids comprise ricinoleic acid, the other approximately 10% of these fatty acids comprise oleic acid, linoleic acid, stearic acid, palmitic acid, and/or dihydroxystearic acid. As is well known in the art, castor oil is produced directly from castor seeds and is hydroxyl functional. In a preferred embodiment, the natural oil component comprises, or is, castor oil. In some embodiments, the castor oil is hydrogenated, while in other embodiments, the castor oil is not hydrogenated.

Other natural oils, which do not have hydroxyl groups, and which have carbon-carbon double bonds, typically require a chemical modification to introduce an active hydrogen-containing functional group. An example is oxidation of carbon-carbon double bonds to functionalize the natural oil with the active hydrogen-containing functional group for future alkoxylation. Any chemical modification known to those skilled in the art may be used to functionalize the natural oil with the active hydrogen-containing functional group. Active hydrogen-containing functional groups, suitable for the present invention, include, but are not limited to, amino groups, hydroxyl groups, carboxyl groups, and combinations thereof. Active hydrogen-containing functional groups provide one or more reaction sites on the natural oil at which polymeric side chains can bond, for example, via the alkoxylation noted above. Other natural oils, suitable for the present invention, include, but are not limited to, canola oil, coconut oil, corn oil, palm oil, peanut oil, soy bean oil, tall oil, and combinations thereof. In a preferred embodiment, the natural oil component comprises or is soy bean oil functionalized to include hydrogen-containing functional groups.

The natural oil component may comprise at least one of monoglyceride, diglyceride, and triglyceride. The natural oil component may include a mixture of differing monoglycerides, diglycerides, and triglycerides. A particularly suitable natural oil component comprises a triglyceride. The chemical formula of the triglyceride is RCOO—CH$_2$CH(—OOCR')CH$_2$—OOCR", where R, R', and R" are alkyl chains. The three fatty acids, RCOOH, R'COOH and R"COOH can be all different, all the same, or only two the same. Chain lengths of fatty acids in naturally occurring triglycerides can be of varying length, but 16, 18 and 20 carbon molecules are common.

The natural oil component may comprise a fatty acid. The fatty acid is typically a carboxylic acid (mono and/or dibasic) having from 7 to 100 carbon atoms, more typically from 10 to 25 carbon atoms, and most typically from 14 to 22 carbon atoms. The fatty acid can be saturated or unsaturated, aliphatic or cycloaliphatic, and/or unsubstituted or substituted with other functional groups such as hydroxyl groups. Suitable fatty acids include, but are not limited to, cetyl acid, lauric acid, linoleic acid, myristoleic acid, oleic acid, palmitic acid, palmitoleic acid, ricinoleic acid, and stearic acid. Mixtures of two or more of the above described fatty acids may be present in the natural oil component. A particularly suitable fatty acid for the present invention is ricinoleic acid.

As mentioned previously, the natural oil polyol is the reaction product of the natural oil component and the alkylene oxide. Because the feedstock is formed from a renewable resource, variations in composition of the natural oil component are common. Without being bound by theory, it is believed that variations in the natural oil component result in variations in the natural oil polyol and structure of the natural oil polyol, and those variations in the natural oil polyol and structure of the natural oil polyol are beneficial to the step of extracting the corn oil.

In many embodiments, the alkylene oxide that reacts with the natural oil component to form the natural oil polyol is selected from the group of ethylene oxide, propylene oxide, butylene oxide, and combinations thereof. In some embodiments, the alkylene oxide that reacts with the natural oil component to form the natural oil polyol is selected from the group of ethylene oxide, propylene oxide, and combinations thereof. In other embodiments, the alkylene oxide that reacts with the natural oil component to form the natural oil polyol is ethylene oxide. Other alkylene oxides including, but not limited to, epihalohydrins, aralkylene oxides, and combinations thereof may be suitable as well. Of course, the invention is not limited to any one of the aforementioned alkylene oxides and any combination of alkylene oxides can be used. However, it is also contemplated that any suitable alkylene oxide that is known in the art may be used in the present invention.

The natural oil polyol of the present invention is formed via alkoxylation. Alkoxylation is a chemical reaction in which the alkylene oxide, such as ethylene oxide and/or propylene oxide, is added to the natural oil component, such as castor oil. The alkoxylation is completed by preheating the natural oil component and reacting it with the alkylene oxide in the presence of a catalyst, such as potassium hydroxide (KOH). Typically, the alkoxylation takes place in a chemical reactor, which is heated and pressurized with nitrogen. However, it is to be appreciated that formation of the natural oil polyol of the instant invention is not limited to any particular chemical reaction. The natural oil component is reacted (e.g. alkoxylated, ethoxylated, etc.) with from about 5 to about 90, alternatively from about 7 to about 60, alternatively from about 10 to about 40, moles of the alkylene oxide.

Typically, the natural oil polyol formed via alkoxylation includes a core, comprising a fatty acid or an ester thereof, and a plurality of polymeric side chains comprising alkyleneoxy groups bonded to the core. The term alkyleneoxy group describes a mer, or unit, of the polymeric side chains. The alkyleneoxy group is the unit which results from the reaction of the alkylene oxide. The plurality of polymeric side chains preferably comprise the alkyleneoxy groups selected from the group of ethyleneoxy groups, propyleneoxy groups, butyleneoxy groups, and combinations thereof. The plurality of polymeric side chains of the natural oil polyol are terminated with a hydroxyl group. The natural oil polyol, which is water soluble in various embodiments depending on the amount and type of polymeric side chain, comprises the core, which is hydrophobic, and also comprises the plurality of polymeric side chains, which are hydrophilic.

The plurality of polymeric side chains of the natural oil polyol are independently selected from the group of polymers having random groups, polymers having repeating groups, and polymers having block groups. The plurality of polymeric side chains of the natural oil polyol may be branched or linear. Furthermore, the plurality of polymeric side chains may be cross-linked with each other. A particularly suitable natural oil polyol has a plurality of side chains, which are linear, and comprise ethyleneoxy groups. Without being bound to any particular theory, it is believed that the plurality of polymeric side chains enables the natural oil polyol to create a "clean boundary" between corn oil and water in the process stream that would otherwise be difficult to achieve. It is believed that the clean boundary allows for separation of more corn oil.

In some embodiments, the natural oil polyol has the following general formula:

$$A_x[(B_y)H]_z$$

wherein

A is derived from a natural oil component;

x is at least 1, alternatively X is 1;

each B is an alkyleneoxy group selected from the group of ethyleneoxy groups, propyleneoxy groups, butyleneoxy groups, and combinations thereof, alternatively ethyleneoxy groups;

y is at least 1, alternatively y is from about 4 to about 20;

z is at least 1, alternatively z is from about 2 to about 3; and

H is a hydrogen atom.

In such embodiments, the natural oil component comprises the natural oil selected from the group of castor oil, soy bean oil, and combinations thereof.

In one embodiment the natural oil polyol comprises a reaction product of castor oil and the ethylene oxide. In this embodiment, the core is branched and the plurality of polymeric side chains are linear and comprise ethyleneoxy groups. The natural oil polyol of this embodiment typically has a hydroxyl value of from about 50 to about 100, mg KOH/g.

In another embodiment the natural oil polyol comprises a reaction product of soy bean oil functionalized to include hydrogen-containing functional groups and the ethylene oxide. In this embodiment, the core is branched and the plurality of polymeric side chains are linear and comprise ethyleneoxy groups. The natural oil polyol of this embodiment typically has a hydroxyl value of from about 20 to about 50, mg KOH/g.

Various embodiments of the natural oil polyol are commercially available from BASF Corporation under the trademark AGNIQUE®.

The process may also include the step of combining the remaining syrup and the wet cake to form WDGS. The remaining syrup is mixed with the wet cake before entering the dryer. The addition of the remaining syrup to the wet cake increases the nutritional value of the WDGS.

Notably, various embodiments of the process can include steps which yield corn distiller's grains, corn distiller's dried grains, DDGS (which contain all of the nutrients of the corn flour minus the starch), corn oil, and corn condensed distillers solubles (generally used to refer to the evaporated co-products produced by the process) of increased quality, e.g. color, the nutritional value because of the use of the alkanesulfonic acid as an alternative to sulfuric acid in one or more steps disclosed.

The DDGS is typically used as animal feed, e.g. to feed cattle, swine, poultry, etc. The color of the DDGS is a quality standard, perceived or real, which can be used to identify DDGS of high nutritional quality, of consistent nutrient content, and/or free of contaminants (mycotoxins dioxin). Specifically, DDGS of homogenous color and a light yellow color is desired.

Color has traditionally been used as a subjective indicator of the nutritional quality of feed ingredients. Free amino acids (especially lysine) can undergo Maillard reactions by combining with reducing sugars, rendering them indigestible by the animal. Maillard reactions occur when sugars and amino acids are heated in the presence of complex carbohydrates and amides. Maillard reactions can occur when the corn derivatives are overheated during the process, and can result in corn oil and DDGS of darker color (browning), burned odor, and burned flavor. In particular, drying temperatures used in dry-milling ethanol plants can range from 127 to 621° C. In addition to being an indicator that a Maillard reaction has occurred, darker color can be an indication of the maturity of the grain, storage conditions, presence of toxins, contamination due to sand, and possible use of insecticides/fungicides.

Color is measured by reading three color characteristics: Lightness or L* (0 dark, 100 lighter), a* (redness-greenness), and b* (yellowness-blueness). As such, the DDGS and the corn oil have a color which can be defined by an L* value, an a* value, and a b* value, i.e., the DDGS has L*a*b* values. L*a*b* values of the DDGS can be measured by a colorimeter/spectrophotometer according to a Hunter Lab color scale. The Hunter Lab color scale is a color-measuring system that is well known to those skilled in the color art. The spectrophotometer employed for measuring the L*a*b* values is typically a 45°/0° spectrophotometer, such as those commercially available from Hunter or X-Rite, although other types of spectrophotometers (e.g. Minolta colorimeters) can also be used. In the Hunter Lab color scale, the L* value is associated with a central vertical axis that represents lightness and darkness, the lightest being L*=100 (white) and the darkest being L*=0 (black). Further, in the Hunter Lab color scale, the a* value is associated with a red/green scale and the b* value is associated with a yellow/blue scale. It is to be appreciated that unlike the L* value, the a* and b* values have no numerical limits. A positive a value is red and a negative a value is green. A positive b* value is yellow and a negative b* value is blue. It is to be appreciated that other color scales can be used to determine the product (e.g. DDGS), such as CIELAB color space. In many embodiments, the DDGS produced by the process has a Hunter L* color score of greater than about 40, alternatively greater than about 45, alternatively greater than about 50, alternatively greater than about 55, alternatively greater than about 60, alternatively greater than about 65, alternatively greater than about 70. In many embodiments, the DDGS produced by the process has a positive b* value when measured on a Hunter Lab color scale.

As is set forth above, the process can include utilizing the alkanesulfonic acid in the steps of: separating corn fiber from the slurry, treating the corn fiber with the composition, and combining the treated corn fiber with the slurry; adding the alkanesulfonic acid to the beer in an amount sufficient to adjust the pH to a range of from about 3 to about 5; distilling the beer to produce ethanol and whole stillage; and extracting corn oil from the syrup. When alkanesulfonic acid is utilized in these steps, it can be utilized with a surfactant, a defoamer, water, a corrosion resistor, and other additives.

Figure 1:
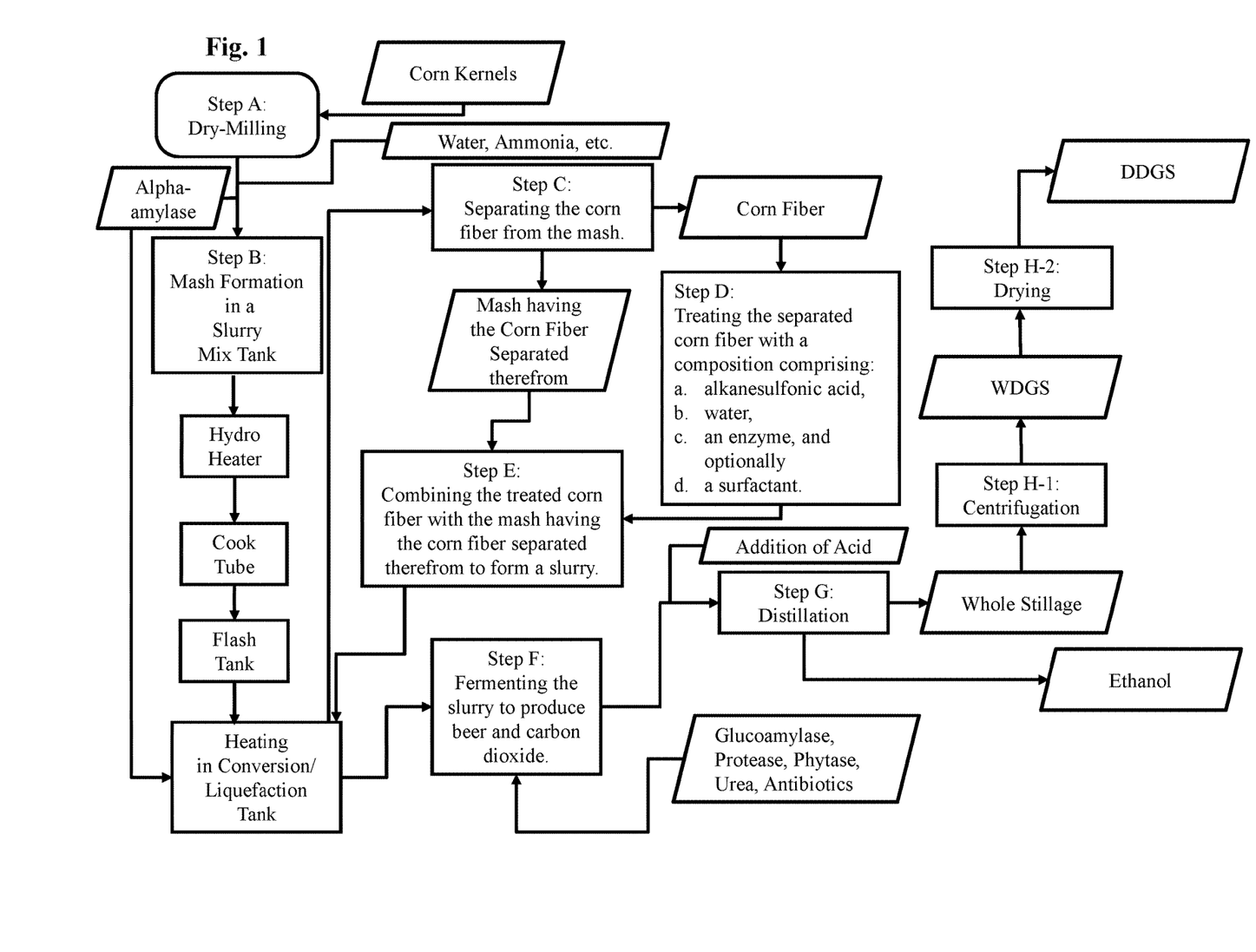
FIG. 1 illustrates a flow chart which diagrams one embodiment of the process of the subject disclosure.

Referring now to FIG. 1, a process in accordance with the subject disclosure is set forth in a flow chart. The process of FIG. 1 includes the steps of: dry-milling corn kernels to form a corn flour comprising corn fiber; combining the corn flour with water to form a mash; separating the corn fiber from the mash; treating the separated corn fiber with a composition; combining the treated corn fiber with the mash having the corn fiber separated therefrom to form a slurry; fermenting the slurry to produce beer and carbon dioxide; distilling the beer to produce ethanol and whole stillage; and processing the whole stillage to produce DDGS. The composition includes an alkanesulfonic acid (e.g. MSA), water, an enzyme(s), and optionally, a surfactant(s).

Figure 2:
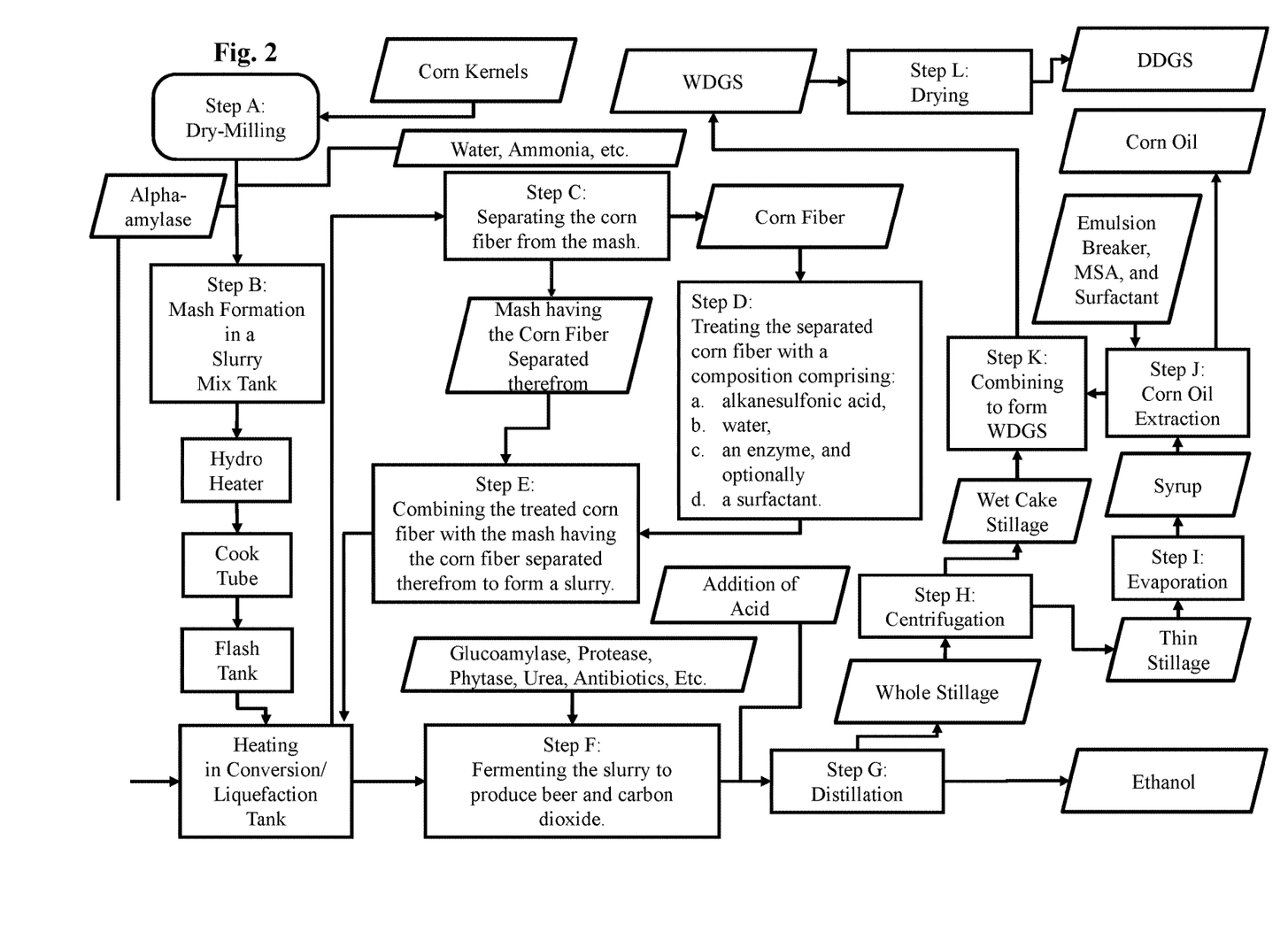
FIG. 2 illustrates a flow chart which diagrams another embodiment of the process of the subject disclosure.

Referring now to FIG. 2, a process in accordance with the subject disclosure is set forth in a flow chart. The process of FIG. 2 includes the steps of: dry-milling corn kernels to form a corn flour comprising corn fiber; combining the corn flour with water to form a mash; separating the corn fiber from the mash; treating the separated corn fiber with a composition; combining the treated corn fiber with the mash having the corn fiber separated therefrom to form a slurry; fermenting the slurry to produce beer and carbon dioxide; distilling the beer to produce ethanol and whole stillage; and processing the whole stillage to produce DDGS. The composition includes an alkanesulfonic acid (e.g. MSA), water, an enzyme(s), and optionally, a surfactant(s). In contrast to the process of FIG. 1, the process of FIG. 2 also includes a "back-end" oil extraction process. More specifically the process of FIG. 2 also includes the steps of: centrifuging the whole stillage to produce wet cake and thin stillage; evaporating water from the thin stillage to form a syrup; extracting corn oil from the syrup; combining the wet cake and the syrup having the corn oil removed therefrom to form wet distillers grain's (WDGS). The step of extracting corn oil from the thin stillage is conducted in the presence of methanesulfonic acid and optionally a surfactant.

The steps of the process can be conducted in-line, as part of a continuous process. Alternatively, the steps can be conducted discretely, one step at a time, with various amounts of time between each step. Typically, the steps of the method are conducted in-line. The steps of the method can be conducted with/in multiple vessels, conveyors, etc. Alternatively, the entire method can be conducted in a single vessel.

The following examples, illustrating the composition and method of the present disclosure, are intended to illustrate and not to limit the disclosure.

Examples

Comparison of the Use of MSA and Sulfuric Acid During Distillation

A beer is produced via the steps of (A) grinding corn kernels to form a corn flour, (B) combining the corn flour with water and an enzyme to form a slurry, (C) heating the slurry to reduce the viscosity, and (D) fermenting the slurry thereby producing beer and carbon dioxide. Steps (A) through (D) are in accordance with the subject disclosure.

In accordance with the subject disclosure, in a Process Example a sample of the beer is distilled subsequent to pH adjustment to 3.5 with methanesulfonic acid (70% by weight MSA in water, e.g., LUTROPUR® MSA). For comparative purposes, in a Comparative Process Example a second sample of the beer is distilled subsequent to pH adjustment to 3.5 with sulfuric acid (96% by weight sulfuric acid in water). In both examples, 250 grams of the beer is acidified with the respective acid to about pH 3.5, i.e. the acid is added to 500 mL in a round bottom flask in an amount sufficient to achieve a pH of 3.5. Table 1 below sets forth the amount of acid required to lower the pH of the beer, and the pH of the beer after the acid is added. For both examples, experiments are conducted in duplicate and the addition of methane sulfonic acid/sulfuric acid is done in parallel under carefully controlled, equivalent conditions.

As set forth above, during distillation, ethanol and whole stillage is produced from beer having a pH of about 3.5. The step of distillation is conducted at 95° C. for a time period of 2 hours. Table 1 below sets forth the amount of ethanol produced in the example processes. The temperature is increased to 105° C. for a time period of 2 hours to remove water. Table 1 below also sets forth the amount of water removed in the example processes.

TABLE 1

| | Acid Amount (g) | | pH of Beer After the addition of the acid | | Ethanol Recovery (g) | | Water Removed (g) | | Process Notes: |
|---|---|---|---|---|---|---|---|---|---|
| | Trial 1 | Trial 2 | Trial 1 | Trial 2 | Trial 1 | Trial 2 | Trial 1 | Trial 2 | |
| Process Example | 1.55 | 1.57 | 3.4 | 3.5 | 33.9 | 29.8 | 62.4 | 65.9 | Minimal Build-up of Organic Material |
| Comp. Process Example | 0.57 | 0.60 | 3.4 | 3.5 | 34.4 | 33.5 | 65.4 | 65.2 | Significant Build-up of Organic Material |

Referring now to Table 1, the ethanol yield of Process Example is comparable to the ethanol yield of Comparative Process Example. Further, the water removed from Process Example is comparable to the water removed from Comparative Process Example. Notably, Process Example has less build-up of organic material in the distillation column allowing for a more efficient process (e.g. less frequent cleaning and better efficiency) than that of Comparative Process Example. From the standpoint of color, the beer of Process Example is lighter/has less color than the beer of Comparative Process Example. As such, Process Example will produce lighter DDGS than the DDGS produced by Comparative Process Example.

After distillation, the whole stillage is cooled. Once cooled, the color of the whole stillage is measured and visually evaluated. The color difference between the whole stillage produced with Process Example Trial 1 and Comparative Process Example Trial 1 is first measured on a Color difference as measured on the Datacolor SF650X standardized with black and white standards, D65 10 degree. The results are set forth in Table 2 below.

TABLE 2

| | C* (Chroma) | h (Hue) |
|---|---|---|
| Process Example (with methanesulfonic acid) | 0.09 | 352.08 |
| Comparative Process Example (with sulfuric acid) | 0.14 | 330.46 |

Referring now to Table 2, lower C* corresponds to less color and higher h value corresponds to lighter hue. As such, the Process Example advantageously produces whole stillage having less color and a lighter hue which produces lighter DDGS than the DDGS produced by Comparative Process Example.

The color of the whole stillage produced with Process Example Trial 1 is also measured via X-rite on a Konica Minolta 2600d hand held spectrophotometer standardized with black and white standards using Comparative Process Example (with sulfuric acid) as a reference. The results set forth in Table 3 below indicate that the whole stillage produced with Process Example has less color than the whole stillage produced with Comparative Process Example.

TABLE 3

| | dL* (D65) | da* (D65) | db* (D65) | dE*ab (D65) |
|---|---|---|---|---|
| Process Example (with methanesulfonic acid) | 1.365 | −0.14 | −0.85 | 1.62 |

In summary, the whole stillage produced with Process Example Trial 1 is lighter than the whole stillage produced with Comparative Process Example Trial 1.

Following distillation, the 50 grams of the whole stillage is centrifuged in a centrifuge tube to produce wet cake and thin stillage, and the thin stillage is then centrifuged. More specifically, the examples are centrifuged at 10,000 rpm and examined for oil separation. After centrifugation, the thin stillage is examined for oil separation, that is, for an oil phase on top of the thin stillage (which is in an aqueous phase).

Corn oil is extracted from the syrup. More specifically, 50 gram samples of whole stillage are centrifuged and separated into a solid phase and a liquid phase. Process Example, Trials 1 and 2, produce more separated oil than Comparative Process Example. Further, Process Example, Trials 1 and 2, produce oil having cleaner separation from the aqueous phase than does Comparative Process Example. The isolated liquid phases are subjected to additional centrifugation to produce an oil phase, an emulsion phase, and a water phase, and the length of these phases is measured on the centrifuge tube. Oil separation results are set forth in Table 4 below.

TABLE 4

| | Emulsion Layer (cm) | | Oil Layer (cm) | | Weight of Oil Recovered | | |
|---|---|---|---|---|---|---|---|
| | Trial 1 | Trial 2 | Trial 1 | Trial 2 | Trial 1 | Trial 2 | Process Notes: |
| Process Example | 0.25 | 0.15 | 0.20 | 0.55 | 0.0922 | 0.4874 | More significant phase separation. |
| Comp. Process Example | 0.40 | 0.25 | 0.10 | 0.20 | 0.0234 | 0.0947 | Less phase separation as evidenced by the lower amount of oil recovered. |

Referring now to Table 4, Process Example yields over 4 times more corn oil than Comparative Process Example without the use of oil extraction aides.

The wet cake and the remaining syrup are then combined to form wet distillers grains ("WDGS"). The WDGS are dried to produce DDGS. The DDGS of Process Example is lighter in color than the DDGS of Comparative Process Example. Lighter colored DDGS is of greater commercial value than darker DDGS.

Use of an Alkanesulfonic Acid During "Front End" Oil Extraction

A sample of mash is produced via dry-milling corn kernels to form a corn flour and combining the corn flour with water. The mash is milled and centrifuged to produce a light phase and a heavy phase. An alkanesulfonic acid is added to the light phase. The light phase is placed in a centrifuge tube and centrifuged to cause the separation of three distinct layers: an aqueous layer, an emulsion layer, and a corn oil layer. The volume (mL) of each layer was measured to calculate the volume percent of each layer. The higher the volume percent of corn oil generated, the more efficient the process.

Comparative Example 1 of the polisher feed was as is, that is, with no additional additive added and therefore non-acidified and having a pH equal to 5.1. Example 1 of the polisher having a pH of 5.1 is combined with LUTROPUR® (R) MSA in an amount sufficient to form a mixture of polisher feed and MSA having a pH to 4.0. Comparative Example 1 and Example 1 were centrifuged.

TABLE 5

| | Comparative Example 1 Polisher Feed, Non-Acidified: pH = 5.1 | | Example 1 Polisher Feed, MSA Acidified: pH = 4.0 | |
|---|---|---|---|---|
| Layer Description | mL | vol % | mL | vol % |
| Corn oil layer | 2.5 | 6% | 7.5 | 15% |
| Emulsion layer | 7.5 | 17% | 5 | 10% |
| Aqueous layer | 35 | 78% | 37.5 | 75% |
| Total | 45 | 100% | 50 | 100% |

Referring now to Table 5 above, the front end oil extraction process of Example 1, which utilizes MSA, yields more than double the amount of corn oil than the front end oil extraction process of Comparative Example 1 which does not utilize MSA. To this end, the use of the MSA in a front end oil extraction process significantly improves the yield of corn oil.

Figure 3:
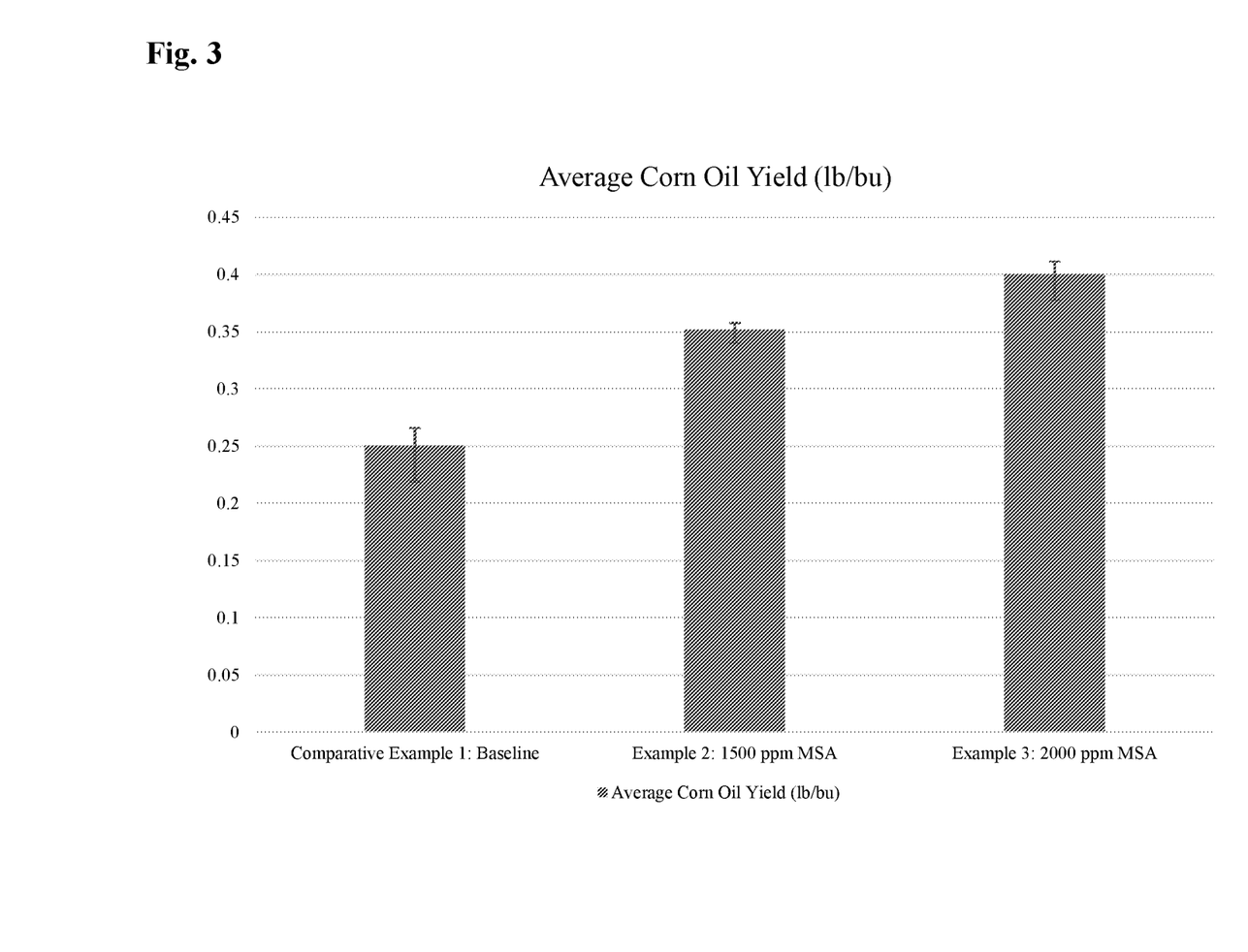
FIG. 3 is a bar chart which shows the average corn oil yield of a front end oil extraction process which can be included in the process of the subject invention.

An example production scale front end oil extraction process is also set forth. A sample of mash is produced via dry-milling corn kernels to form a corn flour and combining the corn flour with water. The mash is milled and centrifuged to produce a light phase and a heavy phase. The corn oil extraction rate on the light phase is then measured (lb. oil/bushel of corn (lb./bu.)) and set forth in FIG. 3. For baseline operation without the addition of an alkanesulfonic acid, e.g. MSA, the average oil production and the upper and lower control limits of oil production are determined and referenced as Comparative Example 2. The average baseline of 0.235 lb./bu. (refer to Comparative Example 2: Baseline in FIG. 3) is measured with upper and lower control limits of 0.266 and 0.250 lb./bu., respectively (refer to bar indicating these values). Upon the addition of 1500 ppm MSA to the polisher centrifuge feed (on the light phase), the average production of corn oil significantly increases by 40% to 0.352 lb./bu. compared (refer to Example 3: 1500 ppm MSA in FIG. 3) and had upper and lower control limits of 0.358 and 0.346 lb./bu., respectively (refer to bar indicating these values). Upon an increase of MSA to 2000 ppm to the polisher centrifuge feed (on the light phase) the average production of corn oil increases by 60% to 0.400 lb./bu. (refer to Example 3: 2000 ppm MSA in FIG. 3) and had upper and lower control limits of 0.411 and 0.389 lb./bu., respectively (refer to bar indicating these values). To this end, the use of the MSA in a production scale front end oil extraction process significantly improves the yield of corn oil.

It is to be understood that the appended claims are not limited to express any particular compounds, compositions, or methods described in the detailed description and the examples set forth therein, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present disclosure has been described herein in an illustrative manner, and it is to be understood that the terminology which has been used is intended to be in the nature of words of description rather than of limitation. Many modifications and variations of the present disclosure are possible in light of the above teachings. The present disclosure may be practiced otherwise than as specifically described within the scope of the appended claims.

What is claimed is:

1. A dry-milling process for the production of dried distiller's grains with solubles (DDGS), said process comprising:
    (A) dry-milling corn kernels to form a corn flour comprising corn fiber;
    (B) combining the corn flour with water to form a mash;
    (C) separating the corn fiber from the mash;
    (D) treating the separated corn fiber with a composition comprising:
        a. alkanesulfonic acid,
        b. water,
        c. an enzyme, and
        d. optionally a surfactant;
    (E) combining the treated corn fiber with the mash having the corn fiber separated therefrom to form a slurry;
    (F) fermenting the slurry to produce beer and carbon dioxide;
    (G) distilling the beer to produce ethanol and whole stillage; and
    (H) processing the whole stillage to produce DDGS.

2. The process of claim 1, wherein the alkanesulfonic acid is present in the composition in an amount of from about 0.1 to about 5 parts by weight based on 100 parts by weight of the composition.

3. The process of claim 1, wherein the enzyme is at least one selected from the group consisting of an acid cellulase, an acid protease, an alpha amylase, a beta glucanase, a glucoamylase, and a xylanase.

4. The process of claim 1, wherein the enzyme is present during the treating (D) of the separated corn fiber in an amount of from about 0.001 to about 0.2, wt. % based on a total weight of the corn kernels.

5. The process of claim 1, wherein the composition comprises at least one surfactant selected from the group consisting of polyalkyleneoxides, alkylpolyalkyleneoxides, polyoxyethylene sorbitan monolaurates, alkylpolyglycosides, anionic derivatives of alkylpolyglycosides, fatty alcohols, anionic derivatives of fatty alcohols, and phosphate esters.

6. The process of claim 5, wherein the composition comprises the alkanesulfonic acid and the surfactant in a weight ratio of from about 10:1 to about 1:1.

7. The process of claim 1, wherein the composition comprises water in an amount of from about 10 to about 95 parts by weight based on 100 parts by weight of the composition.

8. The process of claim 1, wherein the treating (D) of the separated corn fiber with the composition is conducted at a temperature of from about 80 to about 220° C., and a pressure of about 40 to about 4000 kPa.

9. The process of claim 1, wherein the treating (D) of the separated corn fiber with the composition is conducted at a temperature of from about 110 to about 280° C.

10. The process of claim 1, wherein the treating (D) of the separated corn fiber with the composition is conducted at a pressure of from about 100 to about 1600 kPa.

11. The process of claim 1, wherein the treating (D) of the separated corn fiber with the composition is maintained for a duration of less than about 120 minutes.

12. The process of claim 1, wherein the composition is free of sulfuric acid.

13. The process of claim 1, wherein the alkanesulfonic acid is methanesulfonic acid (MSA).

14. The process of claim 1, further comprising adding an alkanesulfonic acid to the beer to adjust the pH to a range of from about 3 to about 5 prior to and/or during the distilling (G) of the beer.

15. The process of claim 1, wherein the distills g (G) of the beer is conducted at a temperature of from about 80 to about 130° C.

16. The process of claim 1, wherein the separating (C) of corn fiber from the mash is conducted with a solids mechanical processor.

17. The process of claim 1, wherein the processing (H) of the whole stillage to form DDGS comprises: centrifuging the whole stillage to produce wet cake and thin stillage; evaporating water from the thin stillage to form a syrup; extracting corn oil from the syrup; combining the wet cake and the syrup having the corn oil removed therefrom to form wet distillers grain's (WDGS); and drying WDGS to produce DDGS having a Hunter L* color score of greater than 40.

18. The process of claim 17, further comprising adding alkanesulfonic acid to thin stillage prior to the evaporating of water from the thin stillage to form a syrup.

19. The process of claim 1, further comprising extracting corn oil from the mash or the slurry via:
  (i) separating the mash or the slurry to produce a light phase and a heavy phase;
  (ii) adding an alkanesulfonic acid to the light phase;
  (iii) extracting corn oil from the light phase; and
  (iv) combining the light phase having the corn oil extracted therefrom with the heavy phase to reform the mash or the slurry.

20. The process of claim 19, wherein the alkanesulfonic acid is methanesulfonic acid (MSA).

21. The process of claim 1, wherein the produced DDGS has a Hunter L* color score of greater than 50.

22. A process comprising:
  dry-milling corn kernels to form a corn flour comprising corn fiber,
  combining the corn flour with water to form a mash,
  separating the corn fiber from the mash with a mechanical processor,
  treating the separated corn fiber with a composition comprising alkanesulfonic acid, water, an enzyme, and optionally a surfactant,
  combining the treated corn fiber with the mash having the corn fiber separated therefrom to form a slurry, and
  processing the slurry to produce ethanol and dried distiller's grains with solubles (DDGS) having a Hunter L* color score of greater than 40.

23. A dry-milling process for the production of dried distiller's grains with solubles (DDGS), said process comprising:
  (A) dry-milling corn kernels to form a corn flour comprising corn fiber;
  (B) combining the corn flour with water to form a mash;
  (C) separating corn fiber from the mash;
  (D) treating the separated corn fiber with a composition comprising:
    a. methanesulfonic acid (MSA),
    b. water,
    c. an enzyme, and
    d. optionally a surfactant;
  (E) combining the treated corn fiber with the mash having the corn fiber separated therefrom to form a slurry;
  (F) fermenting the slurry to produce beer and carbon dioxide;
  (G) distilling the beer to produce ethanol and whole stillage;
  (H) centrifuging the whole stillage to produce wet cake and thin stillage;
  (I) evaporating water from the thin stillage to form a syrup;
  (J) extracting corn oil from the syrup;
  (K) combining the wet cake and the syrup having the corn oil extracted therefrom to form wet distiller's grains with solubles (WDGS); and
  (L) drying the WDGS to produce the DDGS.

* * * * *